United States Patent [19]

Niskanen et al.

[11] Patent Number: 5,079,141
[45] Date of Patent: Jan. 7, 1992

[54] APPARATUS AND METHOD FOR PERFORMING CHEMICAL ANALYSES AND IMMUNOASSAYS

[75] Inventors: Aimo J. Niskanen; Kauko I. Kahma, both of Espoo, Finland

[73] Assignee: Orion Corporation Ltd., Finland

[21] Appl. No.: 379,740

[22] Filed: Jul. 14, 1989

Related U.S. Application Data

[63] Continuation of Ser. No. 863,100, May 14, 1986, abandoned.

[30] Foreign Application Priority Data

May 14, 1985 [FI] Finland .................................. 851915

[51] Int. Cl.⁵ ...................... G01N 33/53; G01N 31/22
[52] U.S. Cl. ................... 435/7.34; 435/7.1; 435/7.32; 435/7.92; 435/7.93; 435/7.94; 435/810; 435/970; 435/975; 436/164; 436/165; 436/169; 436/807; 436/809; 436/810; 422/57; 422/58; 422/61
[58] Field of Search ....................... 435/7.32, 7.34, 7.1, 435/7.92, 7.94, 970, 975, 30, 26, 810; 436/518, 528, 65, 87, 807, 809, 810, 164, 165, 169; 422/57, 58, 61

[56] References Cited

U.S. PATENT DOCUMENTS

| | | | |
|---|---|---|---|
| 3,713,985 | 1/1973 | Astle | 435/810 X |
| 3,826,619 | 7/1974 | Bratu, Jr. et al. | 436/810 X |
| 3,948,606 | 4/1976 | Johnson | 436/809 X |
| 4,090,920 | 5/1978 | Studer, Jr. | 436/810 X |
| 4,225,575 | 9/1980 | Piaso et al. | 436/518 X |
| 4,272,510 | 6/1981 | Smith et al. | 436/809 X |
| 4,299,916 | 11/1981 | Litman et al. | 435/810 X |
| 4,308,028 | 12/1981 | Elkins | 422/58 X |
| 4,496,654 | 1/1985 | Katz et al. | 435/7 |
| 4,594,244 | 6/1986 | Lehner et al. | 435/68 X |
| 4,650,662 | 3/1987 | Goldfinger et al. | 435/810 X |
| 4,657,869 | 4/1987 | Richards et al. | 436/810 X |
| 4,740,475 | 4/1988 | Paul | 422/61 X |
| 4,742,011 | 5/1988 | Blake et al. | 436/518 |
| 4,743,560 | 5/1988 | Campbell et al. | 436/528 X |

FOREIGN PATENT DOCUMENTS

| | | | |
|---|---|---|---|
| 84303021.4 | 11/1984 | European Pat. Off. | 435/7 |
| 2541031 | 3/1977 | Fed. Rep. of Germany | 436/518 |
| 2711634 | 9/1978 | Fed. Rep. of Germany | 422/61 |

Primary Examiner—Esther L. Kepplinger
Assistant Examiner—Carol A. Spiegel
Attorney, Agent, or Firm—Brumbaugh, Graves, Donohue & Raymond

[57] ABSTRACT

The invention comprises a prefilled and presealed apparatus for carrying out chemical, particularly immunochemical, analyses in non-laboratory environments. The apparatus comprises a test base containing therein wells, into which are introduced all the reagents necessary for performing the assay reaction in question. The apparatus further comprises a reagent stick having at one end a sharp reactive point onto which a sample to be assayed can be adsorbed. The base and wells are covered with an impervious foil layer which can easily be pierced with the sharp reactive end of the testing stick included in the apparatus, thereby allowing the adsorbed sample to contact the reagents used in carrying out the assay.

18 Claims, 1 Drawing Sheet

APPARATUS AND METHOD FOR PERFORMING CHEMICAL ANALYSES AND IMMUNOASSAYS

This application is a continuation of application Ser. No. 863,100, filed on May 14, 1986, now abandoned.

FIELD OF THE INVENTION

The invention comprises a prefilled and presealed apparatus containing therein specific reagents for carrying out chemical, particularly immunochemical, analyses in environments other than fully equipped scientific laboratories. With the aid of the invention a chemical analysis can be carried out and the result obtained without any additional equipment at any place whatsoever.

BACKGROUND OF THE INVENTION

Immunochemical analyses, e.g. pregnancy tests, can currently be performed as follows: a sample of material to be tested, such as urine, is pipetted to a first test tube. An analysis stick, to which the material to be tested can bind, is placed in the same tube and incubated for a length of time sufficient to allow material in the urine sample to adhere to the stick. Following incubation of the sample, the stick is removed from the tube and rinsed. The stick is then transferred to a second tube, containing therein a reagent pipetted from a storage bottle, and incubated for a given time. The stick is then rinsed again and added to a third test tube to which a second reagent has been pipetted from a second bottle. The stick is incubated in this third tube for a given time, after which the test result is read as a color indication either from the liquid in the tube or directly from the surface of the stick. A method of this type has been described in the U.S. Pat. No. 4,496,654 and in the patent application EP 84303021.4.

A disadvantage of the methods of the type described above is that the person performing the test must pipet the individual reagents into separate test tubes, which in turn must be supported in a special rack. In practice, therefore, it is possible that the order of pipetting may be incorrect. In addition, the rinse steps must, in many cases, utilize running tap water, which restricts the performance of the assay to the vicinity of a tap dispensing water.

SUMMARY OF THE INVENTION

It is an object of the present invention to provide a plurality of wells prefilled with all reagents required for a particular assay. The apparatus of the invention includes a base made of plastic or some other material impervious to water and the reagents used in the test into which has been molded a sufficient number of wells to contain the reagents required in the analysis. User error is minimized because the wells are filled with the necessary reagents arranged in proper order in the apparatus. The apparatus is then sealed to prevent leakage of the reagents and to maintain the proper order of use. Preferably the sealing material is aluminum foil. Instructions for use of the apparatus, including well number, order of use, and incubation times can be indicated on the sealing material.

To carry out an assay, the apparatus also includes a separate reagent stick made of plastic or some other material onto which the material to be assayed can be adsorbed. The sample is adsorbed to one end of the reagent stick which has a sharp point. The sample contacts the first reagent in the first well by means of the stick piercing the foil over the well. The stick is then left standing in the reagent contained in the well for the requisite length of time for a particular reaction with the adsorbed material to occur. The stick is lifted out of the well and transferred to the reagent in the next well in the series by piercing the foil covering. This procedure is continued until the sample adsorbed to the reagent stick has contacted all the reagents used in the assay.

The invention will be better understood with reference to the specification, accompanying drawings and specific examples.

DETAILED DESCRIPTION OF THE INVENTION

Figure 1:
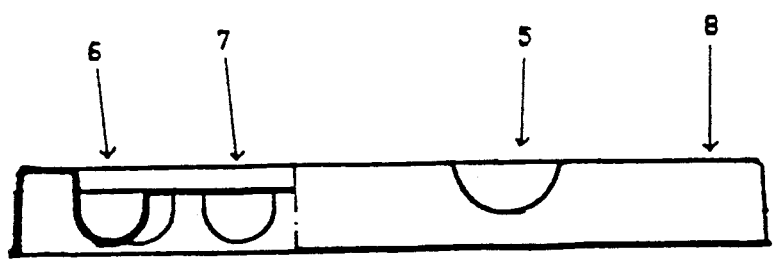
FIG. 1 is a side elevational view, partly in section, of the base of the apparatus.
Figure 2:
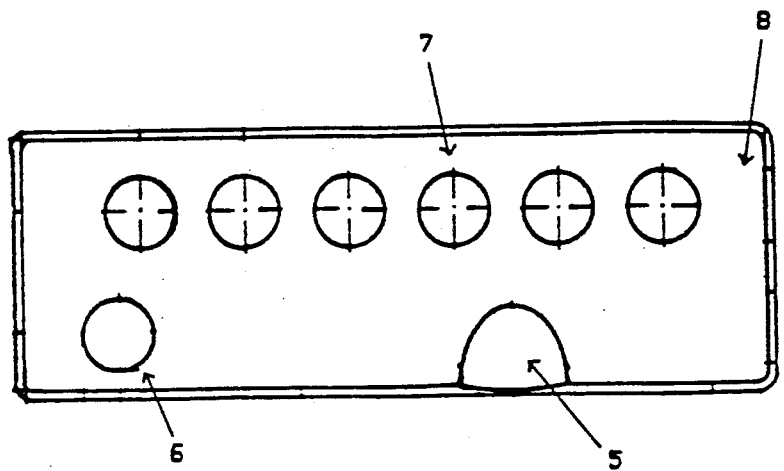
FIG. 2 is a top plan view of the base of the apparatus.

As seen in FIGS. 1 and 2, the base of the test apparatus preferably includes a thumbhold 5 and a rest 6 which holds a sampling spoon described in more detail below in conjunction with FIGS. 3 and 4. The base also contains a series of one or more wells 7 which, when the apparatus is prepared for use in assaying for various biological substances, will contain therein appropriate reagents and rinsing solutions necessary to carry out the assay. The general assay system for which this novel apparatus will find its preferred use is based on the enzyme-linked immunosorbent assay (ELISA). Number 8 in FIGS. 1 and 2 is an indicator to show that the apparatus test base is level. The apparatus test base, including the wells, is constructed of a material which is impervious to the materials used in conducting the assay. Preferably this material should be chemically inert, non-adsorbant of proteins which are present in some of the reagents, and moisture proof.

The test base also should include a protective covering, e.g. of metal foil or the like, which seals the various reagents in the wells 7. Thus in actual practice, the wells 7 may each be filled with the proper reagent and then sealed such that the apparatus may be sold as a ready-to-use kit. Moreover, the sealing covering may have printed instructions or codes to facilitate use of the kit.

Figure 3:
FIG. 3 is a top plan view of a sampling spoon used with the apparatus of FIGS. 1 and 2.
Figure 4:
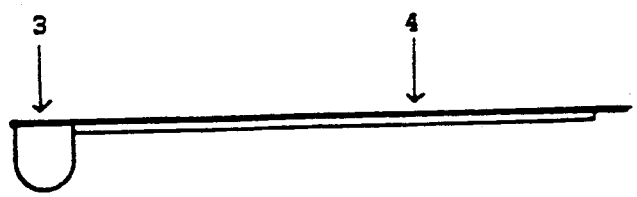
FIG. 4 is a side elevational view of the sampling spoon of FIG. 3.

The sampling spoon shown in FIGS. 3 and 4 is comprised of a sample dish 3 in which the sample to be tested is placed and a stem 4 with which the individual performing the assay can hold the sampling spoon.

Figure 5:
FIG. 5 is a top plan view of a test stick used with the apparatus of FIGS. 1 and 2.

The testing stick shown in FIG. 5 for use with the apparatus comprises at one end a sharp point suitable for piercing the protective covering of the wells and at the other end a stem or handle 2 for manipulation by the operator. The testing stick, and preferably the sharp pointed end 1 which is the reactive end, is prepared from a material to which biological molecules, especially proteins, can adhere. Suitable materials for such purpose include polystyrene, polyvinylchloride, nitrocellulose, glass and paper.

The wells in the test base of the apparatus, as intended for use, contain therein a series of reagents and rinsing solutions in proper order to allow a specific assay to be performed. Preferably, the assay will be of the ELISA-type in which an easily read specific color reaction indicates the presence of a particular substance in the tested sample. In particular, the test base and wells containing therein the reagents for the assay are completely covered with a sealing material impervious to leakage. As noted above, the sealing material preferably will be foil or, more particularly, aluminum foil. Printed directions for use of the apparatus and a numbering system indicating the order in which the wells are to be used can be printed on or attached to this impervious covering.

In use, the apparatus will be provided as a kit which includes the wells filled in the proper order with appropriate reagents and sealed, the testing stick wrapped in a protective covering, and the sampling spoon, also wrapped. The operator does not have to pipet any reagents, thereby minimizing potential error. Instructions for performing the assay may be printed on the sealing material.

For performing an assay using the apparatus of this invention, a plain testing stick or one provided with a precoated antibody, antigen or hapten is incubated for a predetermined amount of time, depending on the assay, in the sample spoon containing a sample of biological fluid to be tested. The length of incubation varies depending on the sample. A testing stick having its pointed reactive end precoated with a specific antibody will adsorb antigens present in the sample with which that antibody reacts. The pointed end of the stick is then pushed through and pierces the covering of the appropriate, and labeled, well in the apparatus which contains a reagent or a rinse solution to wash away non-specifically bound material. Following incubation, the stick, to which the material to be specifically assayed is now adsorbed, is similarly incubated in reagents in each of the successive wells in the series.

The apparatus is especially useful for carrying out an assay system based on the ELISA method in which one of the reagents will be a specific antibody to which an enzyme or other molecule has been conjugated. If the antibody in this conjugate can bind specifically to material adhered to the testing stick the conjugate will also become bound to the stick following incubation. The conjugated enzyme or other molecule is used for detecting the presence of the material of interest from the sample bound to the stick. The last step in the assay is incubation of the stick in a well containing a chromogenic substrate which upon interaction with the enzyme in the conjugate forms a colored reaction product which can be detected on the stick.

The apparatus of this invention therefore can be used to assay body fluids such as saliva, blood, tears, urine, cerebrospinal fluid, and gastric fluids. Specific substances in such body fluids, such as different chemical compounds, including hormones, medical compounds, serum proteins, metabolites and immunoglobulins can be assayed using the apparatus of this invention. Other substances which can be detected using this apparatus include bacteria, viruses, other microbes and parts thereof.

The following examples illustrate the use of the apparatus according to this invention. These examples are merely illustrative and are not intended to limit the invention in any way.

EXAMPLE 1

Assay of *Streptococcus mutans* Bacteria from Saliva Samples

The sharp pointed reactive end of a testing stick coated with antibodies produced against the bacterium *Streptococcus mutans* is incubated in a sampling spoon containing a sample of saliva for 30 minutes at room temperature. *S. mutans* in the saliva sample will bind to the antibody-coated stick. The stick is then removed from the sample, its sharp end pushed through the aluminum foil covering the first well of the test base, and the sample bound to the stick is immersed in he rinsing solution contained in the first well. This step removes any material non-specifically adhering to the testing stick. The stick is then removed from the first well and pushed through the aluminum foil covering the second well. This well contains antibodies produced against the bacterium *S. mutans* and to which molecules of the enzyme alkaline phosphatase have been chemically attached. These antibodies bind to *S. mutans* specifically adhering to the testing stick. The testing stick is kept in this well for 30 minutes, removed and used to pierce the aluminum foil covering the third well of the test base. This well contains another rinsing solution. The stick is removed from the well immediately and used to pierce the aluminum foil covering the fourth well, containing a chromogenic substrate for the alkaline phosphatase enzyme. The alkaline phosphatase enzyme removes the phosphate group from the chromogenic substrate molecule, after which the molecules thus formed react with each other or with other molecules to produce a colored substance, insoluble in water, which precipitates on the surface of the test stick. The stick is held in this well for 10 minutes, removed and examined visually for immediate estimation of the test result. A resulting color reaction indicates the presence of *S. mutans* in the saliva sample.

EXAMPLE 2

Assay of Lutropin from Urine

The sharp pointed reactive end of a testing stick coated with antibodies produced against the $\beta$-subunit of lutropin is incubated in a sampling spoon containing a sample of urine for 10 minutes at room temperature. The stick is then removed from the spoon and its sharp end is used to pierce the aluminum foil covering the first well of the test base, as a result of which sample material adhering to the stick is immersed in the rinsing solution contained in the first well. After this, the stick is removed and pushed through the aluminum foil covering the second well. This well contains antibodies produced against the alpha-subunit of lutropin to which biotin molecules have been chemically attached. The stick is kept in this well for 10 minutes, removed and pushed through aluminum foil covering the third well, containing a second rinsing solution. The stick is removed from the third well immediately and used to pierce the aluminum foil covering the fourth well. This well contains the enzyme alkaline phosphatase to which avidin molecules have been attached by chemical means. Avidin binds specifically to biotin. The stick is kept in this well for 10 minutes, removed and used to pierce the aluminum foil covering the fifth well. This well contains a third rinsing solution. The stick is withdrawn immediately and used to pierce the aluminum foil covering the sixth well. This well contains a chromogenic substrate specific for alkaline phosphatase enzyme. Removal of the phosphate group from the chromogenic substrate by alkaline phosphatase produces a colored compound insoluble in water which precipitates onto the surface of the testing stick. The stick is kept in this well for 10 minutes, removed and examined visually for immediate estimation of the test result. As in the previous Example, the development of a color reaction indicates the presence of lutropin in the urine sample.

We claim:

1. An apparatus for performing chemical analyses and immunoassays comprising
   (a) a base having therein a plurality of wells, each well containing a reagent for use in a multi-step process for detecting the presence of an analyte in a test sample, said base and wells comprising a material impervious to said reagents,
   (b) means for sealing each of said wells so as to retain the reagent therein, said sealing means being a puncturable film or foil, and
   (c) a testing stick having a sharp pointed reactive end comprising a material to which the analyte in the test sample can bind specifically, and which is capable of piercing the sealing means covering said reagent filled wells, such that the reactive end of said testing stick can come into contact with the reagent in the well, thereby allowing the analyte bound to said testing stick to be brought sequentially into contact with the reagents in the wells in order to produce a detectable reaction, thereby detecting the presence of the analyte.

2. An apparatus according to claim 1 wherein the material comprising the sharp pointed reactive end of the testing stick is selected from the group consisting of polystyrene, polyvinylchloride, nitrocellulose, glass and paper.

3. An apparatus according to claim 1 in which the sealing means is aluminum foil on which instructions for use of the apparatus are printed.

4. An apparatus according to claim 1 in which the sharp reactive pointed end of the testing stick is coated with a reagent selected from the group consisting of antibodies, antigens and haptens.

5. An apparatus according to claim 1 wherein the reagents are selected for the assaying of analytes in body fluid.

6. An apparatus according to claim 5 wherein the reagents are selected for the assaying of analytes in body fluid selected from the group consisting of saliva, blood, tears, urine, cerebrospinal fluid and gastric fluid.

7. An apparatus according to claim 1 wherein the analyte is a microorganism.

8. An apparatus according to claim 1, wherein the analyte is selected from the group consisting of hormones, serum proteins, metabolites of physiologic processes, drugs, and metabolites of drugs.

9. A method for performing an immunoassay for detecting the presence of an analyte in a test sample comprising the steps of
   (a) incubating a testing stick having a sharp pointed reactive end comprised of a material to which an analyte in the test sample can bind specifically such that the analyte in the test sample binds to the sharp pointed reactive end of the testing stick;
   (b) inserting in a predetermined order the testing stick of step (a) into a plurality of separately contained reagents for performing an immunoassay and forming a visually or spectrophotometrically detectable complex on the test stick by piercing sealed coverings on reagent-containing wells in a test base with said sharp pointed reactive end of said testing stick;
   (c) allowing said reagents to bind to the analyte on the testing stick whereby a bound detectable complex is formed if the analyte is present in the test sample; and
   (d) visually or spectrophotometrically detecting said bound detectable complex as an indication of the presence of the analyte in the test sample.

10. A method according to claim 9 wherein the analyte is an antigen and wherein the testing stick is coated with an antibody specific to the antigen in the test sample.

11. A method according to claim 9 wherein the analyte is an antibody and wherein the testing stick is coated with an antigen specific to the antibody in the test sample.

12. A method according to claim 9 wherein the test sample is a body fluid.

13. A method according to claim 12 wherein the test sample is a body fluid selected from the group consisting of saliva, blood, tears, urine, cerebrospinal fluid, and gastric fluid.

14. A method according to claim 9 wherein the analyte is a microorganism.

15. A method according to claim 14 wherein the body fluid assayed is saliva and the analyte is *Streptococcus mutans*.

16. A method according to claim 14 wherein the analyte is selected from the group consisting of hormones, serum proteins, metabolites of physiologic processes, drugs and metabolites of drugs.

17. A method according to claim 14 wherein the body fluid assayed is urine and the analyte is urinary lutropin.

18. A method for performing a chemical assay for detecting the presence of an analyte in a test sample comprising the steps of
   (a) incubating a testing stick having a sharp pointed reactive end the surface of which is comprised of a material to which the analyte in the test sample can adsorb such that the analyte in the test sample adsorbs to the surface of the sharp pointed reactive end of the testing stick;
   (b) inserting in a predetermined order the testing stick of step (a) into a plurality of separately contained reagents for performing chemical assay by piercing sealed coverings on reagent-containing wells in a test base with said sharp pointed reactive end of said testing stick;
   (c) allowing said reagents to react with the analyte on the testing stick to produce a detectable product and;
   (d) visually or spectrophotometrically detecting said product as an indication of the presence of the analyte in the test sample.

* * * * *